US006255067B1

(12) United States Patent
Keutmann et al.

(10) Patent No.: US 6,255,067 B1
(45) Date of Patent: Jul. 3, 2001

(54) CDNA ENCODING PEPTIDYL-GLYCINE ALPHA-AMIDATING MONOOXYGENASE (PAM)

(75) Inventors: Henry T. Keutmann, Concord, MA (US); Peter Schofield, Heidelberg (DE); Henry Rodriguez, Belmont, CA (US); Betty Eipper; Richard Mains, both of Baltimore, MD (US)

(73) Assignee: The Johns Hopkins University, Baltimore, MD (US)

( * ) Notice: Subject to any disclaimer, the term of this patent is extended or adjusted under 35 U.S.C. 154(b) by 0 days.

(21) Appl. No.: 07/096,447

(22) Filed: Sep. 15, 1987

(51) Int. Cl.[7] .............................. C07K 14/47; C12N 9/10; C12N 15/12; C12P 21/02
(52) U.S. Cl. ................. 435/69.1; 435/252.3; 435/254.2; 435/320.1; 435/325; 435/349; 530/350; 536/23.5
(58) Field of Search ................................ 435/172.3, 183, 435/69.1, 252.3, 254.2, 320.1, 325, 349; 536/27, 23.5; 935/60, 69, 70, 72, 68; 530/350

(56) References Cited

U.S. PATENT DOCUMENTS 4,708,934 * 11/1987 Gilligan ............................. 435/68.1

FOREIGN PATENT DOCUMENTS 0299790    1/1989  (EP) .

OTHER PUBLICATIONS

Bradbury et al, Nature, vol. 298, 1982, pp. 686–688.
Eipper et al, Proceedings of the National Academy of Sciences USA, vol. 80, (1983), pp. 5144–5148.

Bradbury et al, Biochemical and Biophysical Research Communications, vol. 112, (1983), pp. 372–377.

Bradbury et al, "C–Terminal Amide Formation In Peptide Hormones", Biogenetics of Neurohormonal Peptides, 1985, pp. 171–186.

Murthy et al, The Journal of Biological Chemistry, vol. 261, 1986, pp. 1815–1822.

Murthy et al, Molecular Endocrinology, vol. 1, 1987, pp. 290–299.

Mehta et al., "Purification of a Peptidylglycine alpha–Amidating Enzyme from Transplantable Rat Medullary Thyroid Carcinomas," Arch. Biochem & Biophys. (1988), 261:44–54.

Perkins et al., "Stable Expression of the Catalytic Domain of Bovine Pituitary Peptidylglycine Alpha–Amidating Monooxygenase (PAM) cDNA in AtT–20 Mouse Pituitary Corticotropes," Endocrinology (1989), 124:262a, Abstract 958.

May et al., "Membrane–Associated Forms of Peptidylglycine alpha–Amidating Monooxygenase Activity in Rat Pituitary," J. Biol. Chem. (1988), 263:7550–7554.

* cited by examiner

Primary Examiner—Robert A. Schwartzman
(74) Attorney, Agent, or Firm—Banner & Witcoff, LTD

(57) ABSTRACT

The sequence of bovine PAM is taught as well as new forms of PAM not known before. One new form is membrane bound and provides the basis of methods for alpha-amidating inactive precursors of peptide hormones.

28 Claims, 7 Drawing Sheets

PAM cDNA clones isolated from BIL-4

A. PAM antibody screening

B. Sequencing strategy; relationship of cDNA to peptides and oligonucleotides

FIG. 3A

```
GCGGGCGCTGAGGCGCGCGGGCGCTGCTGTGTGGCCGCCCGCGCCATGAAGTAGCGCGGCTGCGGCGGCGCCGCCTGCGGTCCTCCCGGCCGGGC
         .         .         .         .         .         .         .         .         .
        30        60        90

CGGAGCGCCGAGGACATGGCTGGCTTTCGGAGCCTGCTAGTTCTTCTCCCGTGTTTCCAGTGTGGGCTTCCGAAGCCCACTTCTGTCTTAAGAGGTTTAAAGAAACTACC
         .         .         .         .         .         .         .         .         .
         MetAlaGlyPheArgSerLeuLeuValLeuLeuValPheProSerGlyCysValGlyPheArgSerProLeuSerValPheArgPheLysGluThrThr
        120       150       180       210
                                                    10                  20

AGATCATTTTCCAATGAATGTCTTGTACCACCAGACCAATTCCTATCAGATTTCATCAGATTTTGCGTTGGATATTCGGATGCCTGGGTCACACCCAAACAGTCTGATACGTACTTC
         .         .         .         .         .         .         .         .         .
ArgSerPheSerAsnGluCysLeuGlyThrThrArgProValIleProIleAspSerSerAspPheAlaLeuAspIleArgMetProGlyValThrProLysGlnSerAspThrTyrPhe
        240       270       300       330
                    40                  50                  60                  70

TGCATGTCAGTGCGTTTGCCAATGATGAGGAAGCCTTCGATTGACTTCAAACCCCGTGCCAGCATGGATAATGTCCATCATATGTTTGGATGCAATATGCCAGGCGTCCACT
         .         .         .         .         .         .         .         .         .
CysMetSerValArgLeuProMetAspGluGluAlaPheValIleAspPheLysProArgAlaSerMetAspThrValHisHisMetLeuLeuPheGlyCysAsnMetProAlaSerThr
        360       390       420       450
                    80                  90                 100                 110

GGAAATTACTGGTTTGTGATGAAGGCACCTGTACAGATAAAGCCAATATTCTCTATGCCTGGGCAAGAAATGCTCCCCAACGAGACTCCCCAAAGGTGTTGGATTCAGAGTTGGAGGA
         .         .         .         .         .         .         .         .         .
GlyAsnTyrTrpPheCysAspGluGlyThrCysThrAspLysAlaAsnIleLeuTyrAlaTrpAlaArgAsnAlaProProThrArgLeuProLysGlyValGlyPheArgValGlyGly
        480       510       540       570
                   120                 130                 140                 150

GAGACTGGAAGCAAATACTTTGTACTCCAAGTACACTATGGGATATTAGTGCTTTTAGAGATAATCACAAGGACTGCTCTGGTGTTCCTTACACCTCACACGCCTGCCACAGCCTTTA
         .         .         .         .         .         .         .         .         .
GluThrGlySerLysTyrPheValLeuGlnValHisTyrGlyAspIleSerAlaPheArgAspAsnHisLysAspCysSerGlyValSerLeuHisThrArgLeuProGlnProLeu
        600       630       660       690
                   160                 170                 180                 190
```

FIG. 3B

```
720                            750                               780                               810
ATTGCTGGCATGTACCTTATGATGTCTGTTGACACTGTTATACCACCAGGAGGGAAATGGTGAATTCTGATATTTCATGCCATTATAAAAGTATCCAATGCATGTCTTTGCCACAGA
IleAlaGlyMetTyrLeuMetSerValAspThrValIleProProGlyGlyLysValAlaAsnSerAspIleSerCysHisTyrLysLysTyrProMetHisValPheAlaTyrArg
                              200                             210                             220         ▲▲    230

840                           870                              900                              930
GTTCACACTCACCATTTAGGCAAGGTAGTCAGTGGATACAGAGTAAGAAATGGACAGTGGACCCTGATTGGACGCCAAAGCCCCAACTGCCACAGGCCTTCACCCAGTAGAGCCCCA
ValHisThrHisHisLeuGlyLysValValSerGlyTyrArgValArgArgAsnGlyGlnTrpThrLeuIleGlyArgGlnSerProGlnLeuProGlnAlaPheTyrProValArgPro
                              240                             250                             260                             270

960                            990                             1020                            1050
GTGGATGTGAGTTTTGGTGACATCCTGCAGCAAGATGTGTTCACTGGGGAGGAGGACAGAAGTCACACATTGGTGGCACGTCAGTGATGAAAATGCAACTTATACATTATG
ValAspValSerPheGlyAspIleLeuAlaAlaArgCysValPheThrGlyGluValThrHisIleGlyGlyThrSerSerAspGluMetCysAsnLeuTyrIleMet
                              280                             290                             300                             310

1080                           1110                            1140                            1170
TATTACATGGAAGCCAAGCATGCAGTTTCTTTCATGACCTGTACACAGAATGTAGCTCCAGATATATTCAGAACCATACCACCAGAGCCAATATTCCTGTGAAATCCGATATG
TyrTyrMetGluAlaLysHisAlaValSerPheMetThrCysThrGlnAsnValAlaProAspIlePheArgThrIleProProGluAlaAsnIleProIleProValLysSerAspMet
                              320                             330                             340                             350

1200                           1230                            1260                            1290
GTTATGATGCATGGACATCACAAAGAAACAGAGAACAAAGACTTCTTACTACAGCAGCCCAAACAGGAAGAAGAGTGTTAGAACAGGTGATTCTATTCACTACTTTCC
ValMetMetHisGlyHisHisLysGluThrGluAsnLysAspLysAspThrSerLeuLeuGlnGlnProLysArgGluGluGluValLeuGluGlyAspPheTyrSerLeuSer
                              360                             370            ▲ ▲                380                             390

1320                           1350                            1380                            1410
AAGCTGCTAGGAGAAAGGAAGATGTTGTTCATGCATAAATATAAATCCTACAGAAAAAGGCAGAATCAGAGTCTGACCTGGTAGCTGAGATTGCAAAGTAGTCAAAAGAAGGATCTT
LysLeuLeuGlyGluArgGluLeuPheMetHisValHisValHisLysTyrAsnProThrGluLeuIleAlaAsnValAlaValGlnLysLysAspLeu
                              400               410••••••••    420                              430     ▲
```

FIG. 3C

```
1440                          1470                          1500                          1530
GGTCGGTCCGATACCAGAGAGAGTGCAGAACAGGAGGGCAATGCTATTCTGTCAGAGACAGAATTCACAGAATTCCACAGACTAGTGTCTACCTTGAGGCCTGAGAGAGCAGAGTT
GlyArgSerAspThrArgGluSerAlaGluArgGlyAsnAlaIleLeuValArgGlyIleLysPheHisArgLeuValSerThrLeuArgProAlaGluSerArgVal
                440                           450                           460                           470

1560                          1590                          1620                          1650
CTGTCGTTACAGCAGCCCCTACCTGGTGAAGGCACCTGGAACCAGAACACAGGAGATTCCATGGAGAGGCACTGGATTGGCCTGAGTATACTTGTTACCAGGCCAGGTTTCT
LeuSerLeuGlnGlnProLeuProGlyGluGlyThrTrpGluProGlyGluHisThrGlyAspPheHisValGluAlaLeuAspTrpProGlyValTyrLeuLeuProGlyGlnValSer
                480                           490                           500                           510

1680                          1710                          1740                          1770
GGGGTGGCTCTGGACCCTCAGAATAATCTCGTGATTTTCCACGAGGTGACCACCGTCTCTGGAAACTCTTTTGATAGCAAGTTTGTTTACCAGCAAAGAGGTCTTGGACCAATTGAA
GlyValAlaLeuAspProGlnAsnAsnLeuValIlePheHisArgGlyAspHisValIleTrpAspSerLysPheValTyrGlnGlnArgGlyLeuGlyProIleGlu
                520                           530                           540                           550

1800                          1830                          1860                          1890
GAAGACACTATTCTGTCATAGATCCAAATAATGCTGCAGTACTCCAGTCCAGTGGAAAAAATCTGTTTACTGCCACATGGCTTGAGTATAGATAAAGATGGAAATTATTGGGTCACA
GluAspThrIleLeuValIleAspProAsnAsnAlaAlaValLeuGlnSerSerGlyLysAsnLeuPheThrAlaHisGlyLeuSerIleAspLysAspGlyAsnTyrTrpValThr
                560                           570                           580                           590

1920                          1950                          1980                          2110
GACGTGGCCTTCATCAGGTGTCAAACTAGATCCAAAGAGTAAAGAGGCCCTCTGCTAACCCTGGGAAGGAGCATGCAACCAGGAGTGACCAGAATCACTTCTGCAGCCCACCGAT
AspValAlaLeuHisGlnValPheLysLeuAspProLysSerLysGluGlyLeuLeuThrLeuGlyProLeuLeuThrLeuGlyArgSerMetGlnProGlySerAspGlnAsnHisPheCysGlnProThrAsp
                600                           610                           620                           630

2040                          2070                          2100                          2130
GTGGCTGGATCCAGAGACACCGGAACCATCTATGTCAGATGCTACTGCAACAGTCGCCTTGTCAGTTTTCACCAAGTGAAAATTCATCACACAGTGGAAAATTCATCACACAGTGGGGAGAAGCGTCTAGAG
ValAlaValAspProAspThrGlyThrIleTyrValSerAspTyrCysAsnSerArgLeuValGlnPheSerProSerGlyLysPheIleThrGlnTrpGlyLysPheIleThrGlnTrpGlyLysPheIleThrGlnTrpGlyGluAlaSerLeuGlu
                640                           650                           660                           670
```

FIG. 3D

```
2160                 2190                 2220                 2250
  .                    .                    .                    .
AGCAGTCCTAAACCAGGCCAGTTCAGAGTTCCTCACAGCTTGGCCCTGCCTCCCCTGGCCAGCTGTGTGGCAGACCGGGAAAACGTCGATCCAGTGTTTCAAAACCGACACC
 SerSerProLysProGlyGlnPheArgValProHisSerLeuAlaLeuValProProLeuGlyGlnLeuCysValAlaAspArgGluAsnGlyArgIleGlnCysPheLysThrAspThr
                           680                  690                  700                  710

2280                 2310                 2340                 2370
  .                    .                    .                    .
AAAGAATTGTGCGAGATTAAGCACCATCGTTTGAATTTCATACATACCAGGTTTGCTCTTTGCGGTGAATGAAAAGCCTTACTTTGAGGACCAAGAACCC
 LysGluPheValArgGluIleLysHisProSerPheGlyArgAsnValPheAlaIleSerTyrIleProGlyLeuPheAlaValAsnGlyLysProTyrPheGluAspGlnGluPro
                           720                  730                  740                  750

2400                 2430                 2460                 2490
  .                    .                    .                    .
GTGCAAGGATTTGTGATGAACTTTTCAGCGGGGAAATTATCGATGTCTTCAAGCCAGTTGCGCAAGCACTTGACATGCCCCACGACATTGCGGAGGACGGAGACCGTATGTC
 ValGlnGlyPheValMetAsnPheSerSerGlyGlyGluIleIleAspValPheLysProValArgGlnHisPheAspMetProHisAspIleAlaAlaSerGluAspGlyThrValTyrVal
                   760 ●●●●●●●●●       770                  780 ▲▲              790

2520                 2550                 2580                 2610
  .                    .                    .                    .
GGAGACGCTCACACCAACACCGTGTGAAGTTCACCTGACCGAAAAATGAACATCAGTCAGTTCAGGAAGCTGGCATTGAGGTTCAGGAAATCAAAGAATCGAGGCAGTTGTTGAA
 GlyAspAlaHisThrAsnThrValTrpLysPheThrSerThrGluLysMetGluHisArgSerValLysLysAlaGlyIleGluValGlnGluIleLysGluValValValGlu
                   800                  810                  820 ▲▲          830

2640                 2670                 2700                 2730
  .                    .                    .                    .
ACCAAAATGGAGAACAAGCCCCTCCTCAGAATTGCAGAAGATACAAGAGAAACAGAAGCTGTCAAAGACCGGCTCGAGTGCCGTGTTCTCATTACAACCCTTCTGTTATT
 ThrLysMetGluAsnLysProLeuLeuArgIleAlaGluAspThrArgGluThrGluAlaValLysAspArgLeuGluCysArgValLeuIleThrThrLeuLeuValIle
                   840                  850                  860                  870

2760                 2790                 2820                 2850
  .                    .                    .                    .
CCTGTGGTTGTCCTGCTGGCCATTGCCTTATTATTCGGTGAAAAATCAAGGGCCTTTGAGATTCTGAACGTAAACTTGAGGCCAGTTGAACGTAAACTTGAGGCCAGTTGAAGAGA[GATTCTGGAAGAGTTCTGGAAGACTTAGAGGA
 ProValValLeuAlaIleAlaLeuPheIleArgTrpLysLysSerArgAlaPheGlyAspSerArgAlaPheGlyAs]pSerArgAlaPheGlyLeuAlaSerSerGlyArgValLeuGlyArgLeuArgGly
                   880                          ▲         900▲                            910
```

```
2880                              2910                              2940                              2970
AAGGGAGGCGGAGGCCTAAACCTGGGCAACTTCTTCGCCAGCCGGAAGGGCTACAGCCGGAAGGGTTCGACCCGCCCTCAGCCGGAAGCACGAAGCCGACCAGGAAGATGAGGACCAAGC
LysGlyGlyGlyGlyLeuAsnLeuGlyAsnPheAlaSerArgLysGlyTyrSerArgLysGlyPheAspArgLeuSerThrGluGlySerAspGlnGluLysAspGluAspAlaSer
                              920                                                            940                     950
                                                                                      ▲▲▲
3000                              3030                              3060                              3090
GAGTCCGAAGAAGAGTACTCGGCCCCGCCCCCCGCCCCCTGCCCTCCTGAGAAACTGGGTTTTCTTTAGGCTGACGAGACTTACCAAGGATGCCAGTTCCTTCCCCTTGAGCA
GluSerGluGluTyrSerAlaProProProAlaProSerSer
                              970

3120                              3150                              3180                              3210
CGTTGAGCGGTTTGCGTATTTAACTGTAAACTGTACCCATCTGTGTGGACCGTACACCCTTTATTTACTTCCTTTGGGATTAGTTGGCTTCGTTCCTAGTGAGGAGTTTCCTGAAAG 3240                              3270                              3300                              3330
TTCATTCATCGTGCCATTGTCTTTATATGAACATAGGCTAGAGAAGTGATCCTCTTCCGTCACAGTCACTTAGGGATGAAGTTTGCTCATCTGCATTTCTGAGACTTTTCTG 3360                              3390                              3420                              3450
TAGTTTGTAAATAACTCCATTCTGCTTGAACACAGTATTCTCCCAGTAGCACTTCCATTGCCAGTGTCTTCTTCTTGGTGCCTTTCCTGTTCAGCATTCTCAGCCTGTGGCAGTGAAGA 3480                              3510                              3540                              3570
GAAACTTTGTGCTACATGACAACAAAGCTGCTAAATCTCCTATTTTTTAAAATCACTAACATTATTGCAACAAGGGAAAGAAAAAGTCTCTATTTAAATTGTTTTTTTTAATTT 3600                              3630                              3660                              3690
CCTTCCTCAGTTGGTGTGTTTGGGATGTCTTATTTTTAGATGGTTACACTGTTAGATCACTATTTTCAGAATCGAATGTAATTGTGTAATAAGTGTTTTCAGAGCATTAATAAAAAA

3720
AAAAAA
```

FIG. 3E

CDNA ENCODING PEPTIDYL-GLYCINE ALPHA-AMIDATING MONOOXYGENASE (PAM)

This invention was made using grants provided by the National Institutes of Health. The Federal Government may retain certain rights in this invention.

TECHNICAL AREA OF THE INVENTION

The field of this invention is post-translational processing enzymes, more particularly the enzyme known as peptidyl-glycine alpha-amidating monooxygenase (PAM).

BACKGROUND OF THE INVENTION

Small, biologically active peptides are frequently produced as larger, usually inactive precursors (preprohormones). Specific proteolytic cleavages liberate various peptides from these precursors. A variety of covalent modifications of the precursor molecule and the smaller peptides occur following synthesis of the preprohormone. One such modification is alpha-amidation, in which the carboxy-terminal carboxylic acid group of a peptide becomes blocked with an alpha-amide group. Approximately half of all known bioactive peptides contain amide groups at their C-termini. In most cases, unblocked versions of these peptides are much less active (on the order of 0.1 to 1%) than their amidated derivatives.

While it is possible to synthesize by chemical means small peptides which contain an amide group at the C-terminal end (alpha-amide), larger alpha-amidated peptides are difficult and expensive to produce. Larger peptides are often produced by expression in bacteria or yeast, but these microbes have not been shown to contain enzymes which can catalyze peptide alpha-amidation of expressed peptides. Thus many peptides produced in cultured microbial cells require the action of PAM to achieve full activity.

PAM activity has been detected in porcine, bovine, human and rat pituitary as well as in other species and tissues, such as frog skin. Some of these PAM enzymes have been purified or partially purified. See, for example, Murthy, et al., Journal of Biological Chemistry, Vol. 261, pp. 1815–1822 (1986) and Mizuno, et al., Biochem. Biophys. Res. Comm., Vol. 137, pp. 984–991 (1986). Prior art purification methods of PAM activity have been directed to soluble enzymes from tissue extracts. This has led to the identification of proteins of approximate molecular weight of 60,000 in porcine pituitaries and molecular weights of 38,000 and 54,000 from bovine pituitaries. However, studies have shown that there is very little PAM protein isolatable from natural sources such as bovine and porcine pituitaries. Thus there is a need in the art to obtain a ready source of PAM enzyme.

SUMMARY OF THE INVENTION

It is an object of the present invention to provide a DNA isolate which encodes a PAM enzyme.

It is an object of the present invention to provide a DNA vector which encodes a PAM enzyme.

It is another object of the present invention to provide PAM proteins containing membrane spanning domains.

It is yet another object of the present invention to provide a method for producing a PAM enzyme in cultured cells.

It is still another object of the present invention to provide a method of activating peptide hormone precursors to their mature amidated forms using a PAM preparation.

These and other objects are provided by one or more of the following embodiments of the present invention. In one embodiment a DNA vector is provided which encodes a PAM enzyme. In another embodiment a DNA isolate is provided which encodes a PAM enzyme.

In another embodiment, a method of producing a PAM enzyme is presented which comprises providing cultured cells which can replicate and express an intron-free coding sequence of a PAM enzyme, growing said cultured cells, and recovering the PAM produced from said cultured cells. The transformed cells themselves are also contemplated by the present invention.

In yet another embodiment of the present invention PAM proteins comprising a membrane spanning domain are provided which are substantially free of other proteins which do not have PAM activity.

In yet another embodiment of the present invention an in vitro method is provided of activating a hormone precursor to produce a mature hormone having an alpha-amide group on the C-terminal amino acid residue, said method comprising, providing a peptide hormone precursor having a glycine residue on the C-terminal side of the C-terminal amino acid residue of the mature hormone, and contacting said peptide hormone precursor with a membrane preparation having PAM activity to form an alpha-amidated derivative of the peptide hormone.

The present invention provides the art with a ready source of PAM protein similar to that purified from natural sources (e.g., pituitary) as well as its precursor forms and a membrane associated form. By producing PAM protein in cultured cells, one can obtain much larger amounts of protein than are currently practicably available from natural sources. In addition, the existence of a membrane associated form of the PAM enzyme allows for the use of immobilized PAM enzyme in the in vitro maturation and processing of genetically engineered hormones and bioactive peptides.

BRIEF DESCRIPTION OF THE DRAWINGS

FIG. 3 is a schematic which depicts the key features of the complete PAM protein.

DETAILED DESCRIPTION

Figure 1:
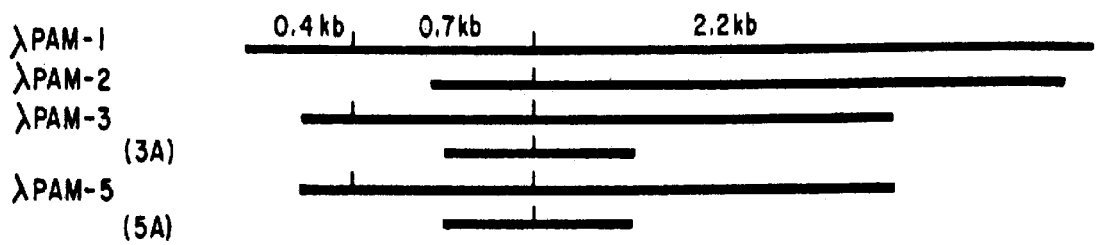
FIG. 1 depicts the lambda-PAM clones obtained by screening a cDNA library (first with PAM antibodies and then with fragments of PAM cDNA) and depicts the sequencing strategy used to obtain the DNA sequence.
Figure 1:
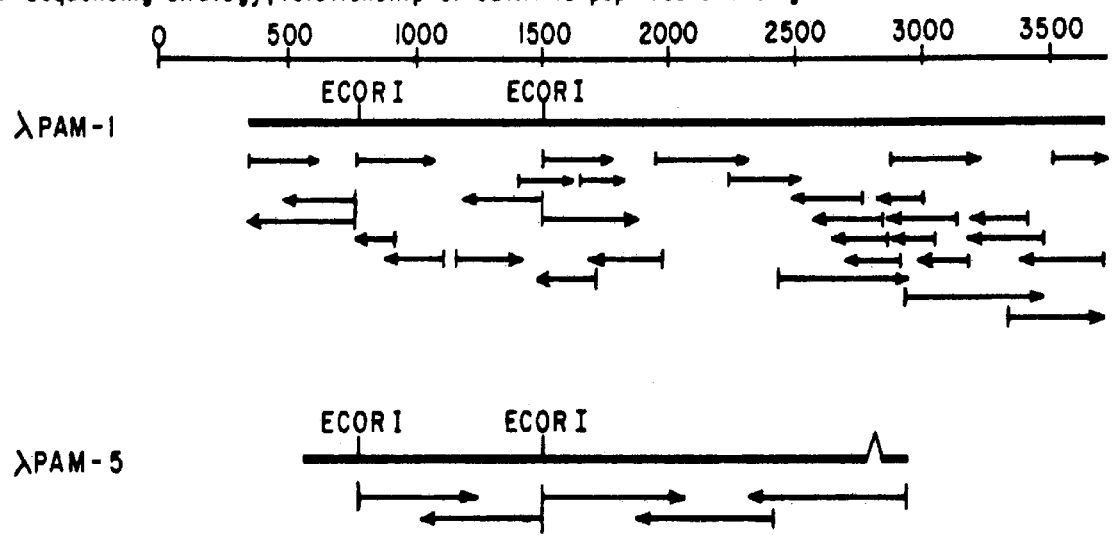
Figure 1:
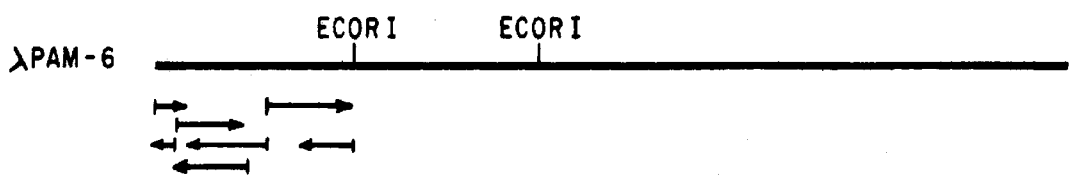

It has been discovered that a gene encoding PAM in cows produces a protein more than twice as large as either of the two bovine PAM proteins previously purified. The previously purified bovine PAM proteins, PAM-A and -B, are soluble enzymes obtained by homogenizing frozen neurointermediate pituitary tissue in an aqueous buffer and centrifuging to remove the particulate matter. One form of PAM protein disclosed herein is membrane associated; the existence of this form of the protein was unanticipated and unexpected.

Other features of the large PAM protein have been deduced from studying the complete cDNA sequence of a PAM gene. These features include a hydrophobic signal sequence, probably comprising the first twenty amino acids of the protein. Additionally, there are two potential endoproteolytic cleavage sites which account for the two populations of PAM N-termini observed experimentally. These cleavages occur after $Arg^{30}$ and $Arg^{36}$. The segment of protein between $Phe^{21}$ and the N-terminal residues of the mature PAM proteins represents a "pro-peptide", removed following cleavage of the signal sequence. The effect of the pro-peptide on enzyme activity is as yet unknown.

Generation of the C-termini of PAM-A and PAM-B could result from endoproteolytic cleavage at pairs of basic amino acids located at residues numbered 432 and 378, respectively. Such cleavages would lead to proteins of predicted molecular weights 45,000 and 39,000, respectively. The segment of amino acids between residues 379 and 432 is acidic. This property of the segment is consistent with the fact that PAM-A binds to DEAE-cellulose at neutral pH while PAM-B does not.

Additional features of the PAM enzymes which are apparent from the DNA sequence are the two clusters of histidine residues at residues numbered 240 and 360 which may be involved in copper binding.

The membrane spanning or transmembrane domain of the protein consists of an extremely hydrophobic twenty-four amino acid segment running from residues 864 to 887. The calculated hydrophobicity index for the domain is 2.9. Any peptide segment of this length with a hydrophobicity index greater than 1.6 is highly likely to be membrane-spanning. Kyte, et al., J. Mol. Biol., Vol. 157, pp. 105–132 (1982); and von Heijne, Eur. J. Biochem, Vol. 120, pp. 275–278 (1981). Substantial amounts of membrane associated PAM activity have been found in accordance with this invention in mouse corticotrope tumor cells and rat anterior pituitary; lesser amounts of membrane-associated PAM activity have been found in rat neurointermediate pituitary. The existence of membraneassociated PAM activity is consistent with the occurrence of a membrane spanning domain in the bovine protein, which is predicted from the cDNA sequence. The tissue-specific distribution of PAM activity amongst soluble and particulate fractions was unexpected.

Immediately following the transmembrane domain is a cluster of basic amino acids (residues 888–893). This feature is characteristic of the cytoplasmic side of transmembrane domains and is thought to serve as a stop transfer signal. Kyte, supra and von Heijne, supra. Two forms of this region have been detected, one (lambda PAM-1) having eighteen amino acids more than the other (lambda PAM-5). This heterogeneity is most likely due to alternative splicing sites in the mRNA. Alternatively, this difference could reflect a polymorphism in the population of cows used to make the cDNA library. The remainder of the protein until the C-terminus is probably cytoplasmic.

There is a 430 residue region of the primary translation product which is between the PAM-A carboxy-terminus and the transmembrane domain. Two pairs of basic amino acids occur in this region as well as a potential site for N-linked glycosylation at $Asn^{762}$-Phe-$Ser^{764}$. This region could contribute to the stability of the protein, or to its aggregation. It also provides a potential region with which to crosslink the protein to other substances, such as resins, without impairing enzymatic activity.

The cDNA sequences of the present invention are intron-free because they have been obtained by reverse transcription of mRNA. The transcribed mRNA was mature and therefore intervening sequences had already been removed. The PAM gene in the bovine chromosome contains numerous introns.

The PAM coding sequences of the present invention include any which produce a protein having the desired alpha-amidating enzymatic activity. These may include the PAM-A and PAM-B proteins, as well as other forms containing, for example, the signal sequence, the pro-peptide sequence, the membrane spanning domain and/or the cytoplasmic domain. PAM-A is the larger form of the soluble enzyme having an apparent molecular weight of about 54,000 from gel filtration measurements and a predicted molecular weight of about 45,000 from the nucleotide sequence. PAM-B is the smaller form of the enzyme, having an apparent molecular weight of about 38,000 and a predicted molecular weight of about 39,000. The signal sequence is the hydrophobic segment immediately following the initiator methionine which is used to translocate nascent proteins across the membrane of the organelle in which they are synthesized. These signal sequences are generally cleaved from the protein after they have been translocated. The signal cleavage in the PAM precursor protein probably occurs between $Gly^{20}$ and $Phe^{21}$.

The N-terminus of mature PAM-B was determined by amino-acid sequencing. The population of PAM-B appeared to be heterogeneous, yielding two amino acids at each cycle. One form of the protein begins with $Phe^{31}$ and the other with $Ser^{37}$. This heterogeneity is probably due to different endoproteolytic cleavages, after $Lys^{29}Arg^{30}$ and after $Arg^{36}$. The short region between the signal sequence and the N-terminal residues of PAM-B represents a pro-peptide which is removed following the cleavage of the signal sequence.

The primary translation product of the PAM mRNA comprises all of these regions described. Post-translational endoproteolytic cleavages lead to the various forms of PAM observed in tissues. Some of these various forms of soluble PAM could well explain the reports in the literature of broadly eluting activity peaks from gel filtration columns. A full length mRNA sequence is one which codes for all of the primary translation product. This mRNA is mature in that its intervening sequences have been removed by splicing.

Figure 2:
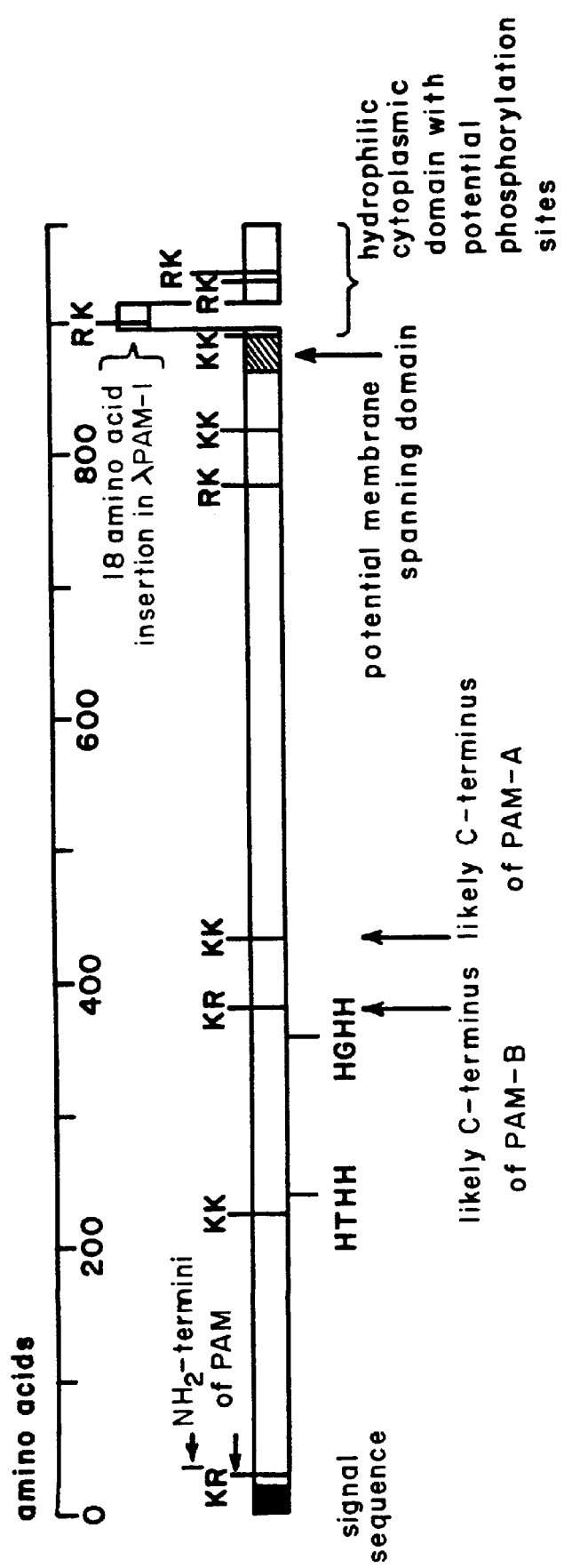
FIG. 2 shows the complete nucleotide sequence of PAM cDNA.

PAM-encoding DNA sequences can be obtained according to the sequence shown in FIG. 2. The sequence may be chemically synthesized. Alternatively, short segments of at least about 30 nucleotides can be synthesized and used as hybridization probes to genomic or cDNA libraries. Such libraries can be prepared from any species encoding and/or expressing PAM activity, including rat, cow, mouse, and human. Thus both intron-free and intron-containing sequences may be obtained which encode a PAM enzyme. Means for chemical synthesis of DNA sequences and hybridization are well known in the art. Means of making genomic and cDNA libraries are also well known. See, for example, *Molecular Cloning,* Maniatis et al., Cold Spring Harbor Laboratory, 1982.

An expression vector can be made by inserting the coding sequences of PAM in a suitable vector. Suitable vectors have promoters for initiating transcription just upstream from the insertion site of the PAM sequences. Suitable promoters are known in the art and will be selected for their functional characteristics in the host cell. For example, the mouse metallothionein promoter and the SV-40 small T promoter may be used for mouse and monkey cells, respectively. Bacterial promoters may be used for production of PAM in bacteria. Downstream from the site of insertion of the PAM sequence a poly-A signal is desirable. This may derive from either the PAM sequences or from another gene. Also desirable in the vector are selectable markers, such as drug resistance markers. A particularly desirable marker is a bacterial aminoglycoside phosphotransferase gene which can detoxify both antibacterial (e.g., neomycin) and anti-eukaryotic cell (e.g., G418) agents.

A DNA isolate which encodes a PAM enzyme, as used herein is a molecule which has been extracted from a living cell and substantially purified from other non-PAM coding sequences. Alternatively a DNA isolate may be a molecule which has been chemically synthesized according to the PAM sequence taught herein and not containing coding sequences for other proteins. A DNA vector, as used herein is a molecule which can replicate in some species. It thus provides a means of biologically producing PAM DNA sequences. DNA vectors are produced by genetic manipulation, either using recombinant DNA techniques in vitro or in vivo. Thus naturally occurring chromosomes, for example, are not encompassed by this term. One such DNA vector is a lambda phage carrying the entire coding sequence of the primary translation product of bovine PAM (lambda PAM-6) in a lambda gt 11 vector. Another such vector, Mt.PAM-1, contains the entire PAM coding sequence downstream from a mouse metallothionein promoter. It also contains ampicillin and G418 resistance genes and a bacterial origin of replication. In addition, an SV40 poly-A site and splice site are present, isolated from the small T antigen gene.

Cultured cells which can be used in the practice of the invention for expressing a PAM protein may be any which can replicate and express an intron-free coding sequence of a PAM enzyme. In general, the cells will be chosen for the rate of production and cost of production of active PAM proteins. Possible desirable characteristics of the cells to be considered include provision of a stable environment for the PAM protein, secretion of PAM, formation of membranes rich in PAM, glycosylation and/or phosphorylation of PAM, faithful endoproteolysis of PAM. All of these characteristics may not be desirable for a particular purpose and may even be mutually exclusive. For some purposes prokaryotic microorganisms such as $E.$ $coli$ may be used; for other purposes eukaryotic microbes such as $S.$ $cerevisiae$ may be used; still other applications may require tissue culture cells. Tissue culture cells may include avian or mammalian cells, such as mouse, rat and monkey cells. Expression may be transient or continuous depending on the integration of the PAM gene. Choice and use of these cell systems is within the skill of the ordinary artisan.

The peptide hormones which are activated by PAM are neuronal and endocrine peptides which are bioactive. That is, they usually affect the functioning of cells other than the producing cells. Approximately half of the known neuronal and endocrine peptides have an alpha-amidated amino acid at their carboxy-terminus which is essential for activity. These include gastrin, neuropeptide Y, vasopressin, and corticotropin releasing factor. In every case where the amino acid sequence of the precursor molecules has been determined, a glycine has been found to follow the residue that is amidated in the mature peptide. Glycine appears to be mandatory in the substrates for PAM as the amino group donor, vicinal to the amino group receptor residue. Novel amidated peptides are being discovered in many tissues and it is anticipated that their production requires the action of PAM.

The membrane preparations used in the practice of the present invention may be synthetic or natural. That is to say that purified PAM protein having a membrane spanning domain may be incorporated into membranes such as liposomes, or natural membranes, for example, from bacterial or animal sources. Methods for preparing membranes are known in the art. See, e.g., Rengasamy A. et al., Biochem. Biophys. Res. Comm., Vol. 126, pp. 1–7 (1985). Methods for preparing liposomes are also known. See, e.g., Szoka et al., Proc. Nat. Acad. Sci. U.S.A., Vol. 75, pp. 4194–4198 (1978). Alternatively, cells which produce PAM and incorporate PAM into their membranes, such as mouse corticotrope tumor cells and rat anterior pituitary cells, may be used as a source of membrane preparations having PAM activity. Yet another source of membrane preparations is a cultured cell which can replicate and express an intron-free coding sequence of PAM. Use of membrane bound PAM may provide benefits such as ease of product separation and purification, as well as increased stability of PAM activity.

When $E.$ $coli$ are infected with lambda phages PAM -1, -2, -3, or -5 and treated with IPTG (isopropyl-beta-D-thiogalactopyranoside), PAM protein sequences are expressed. (See Example 2, below for precise description of construction and FIG. 1 for maps.) The expressed proteins are fusion proteins of $E.$ $coli$ beta-galactosidase and bovine PAM sequences. Thus these infected cells are an example of cultured cells which are able to replicate and express an intron-free coding sequence of a PAM protein. There are numerous other possible cultured cells for producing PAM protein and active PAM enzyme. An appropriate vector is required for the particular cells to effect replication and expression. Many such vectors are known in the art.

The mRNA and genes for PAM from many animal species can be identified using DNA probes derived from any of the lambda PAM phage or synthesized according to the bovine PAM sequence presented in FIG. 2. These DNA probes can be used to identify clones encoding PAM from a cDNA library derived using RNA of various animal species and various tissues. These probes can also be used to identify PAM clones in genomic libraries. These probes will generally be from about 60 to 5000 nucleotides in length, and can be synthesized or isolated from organisms. The probes may also be used to study the expression of PAM in various organs of the same animal. For example, probes derived from the 0.7 and 2.2 kilobase fragments of lambda PAM-1 were used to determine expression levels in various rat tissues. The probes detected highest levels of PAM mRNA expression in rat neurointermediate pituitary lobes, cerebral cortex and hypothalmus, lower levels in anterior pituitary, and no detectable PAM mRNA in the liver. These probes also were able to detect mRNA in mouse corticotropic tumor cells. In addition these probes have been used to identify homologous restriction fragments in digests of bovine, human, rat and mouse genomic DNA.

Once the PAM cDNA of another animal species has been obtained, as described above, expression vectors for the PAM proteins can be constructed. These may be employed in suitable cultured cells to obtain expression of the PAM proteins. Many techniques for constructing such vectors are known in the art.

To obtain a PAM protein having a membrane spanning domain, substantially free of other proteins, a number of approaches may be used. The protein may be obtained from natural sources such as animal pituitaries, but only small amounts of protein could be expected. Alternatively, membrane associated PAM could be purified from cultured cells which replicate and express the full length PAM coding sequence. Because of the large portion of the protein not present in PAM-A or -B, this membrane associated PAM protein will behave differently on most chromatographic columns from PAM-A or PAM-B. However, antibodies raised against PAM-A or PAM-B or PAM- beta-galactosidase fusion proteins can be used to identify the large PAM protein. Other physical properties, such as size and charge, can be used to separate the large PAM protein from PAM-A or PAM-B. In addition, affinity purification methods, which have been used for PAM-A and PAM-B should also be successful. Other protein purification means are known in the art and can also be used in this context.

In order to amidate proteins efficiently using PAM enzymes, the reaction conditions should be optimized. Various forms of PAM may display different physical properties and may require different co-factors. PAM-A and PAM-B both exhibit pH optima at alkaline pH. In addition, their activities are stimulated by the addition of molecular oxygen, copper and ascorbate.

The following examples are intended to illustrate the invention and not to limit or define the invention.

EXAMPLE 1

This example demonstrates that the protein purified from bovine neurointermediate pituitary corresponds to the enzyme activity sought, i.e. peptidyl-glycine alpha-amidating monooxygenase.

PAM-A and PAM-B were purified as described in Murthy et al, Journal of Biological Chemistry, Vol. 261, pp. 1815–1822 (1986). Polyclonal PAM antiserum (Ab 36) was generated by subcutaneous injection of a rabbit with 9 ug PAM-B dissolved in 0.9% NaCl, 0.75% SDS, by boiling and emulsified with complete Freund's adjuvant; the rabbit was boosted once with a similar sample of PAM-B and twice with a mixture of PAM-A plus PAM-B. Pooled, purified PAM-A and PAM-B from 400 bovine neurointermediate pituitaries were linked to 350 mg activated CH-Sepharose 4 B (Pharmacia). Antiserum was affinity purified as described in Wand et al, Endocrinology, Vol. 120, pp. 953–961 (1987). The purified antibody was bound to a Protein A resin.

To avoid confusion due to the PAM activity in rabbit serum, an enzyme depletion assay was used. The purified PAM-B was spiked with radioiodine-labeled PAM-B protein. The spiked mixture was incubated with the anti-PAM resin. The resin was then separated from the supernatant. The radioactivity bound to the resin was determined, as was the amount of enzyme activity remaining in the supernatant. Similar incubations and determinations were performed using various amounts of antibody resin.

The results showed a linear relationship between the depletion of PAM activity from the supernatant and the appearance of radiolabeled protein bound to the resin. This result is consistent with the identity of the enzyme activity and the major protein.

EXAMPLE 2

This example shows how PAM cDNA clones were obtained and PAM DNA fragments mapped. Antiserum (Ab 36) was prepared as above.

In order to prepare the cDNA library, the procedures of Snyder et al, Methods in Enzymology, Vol. 155, part F (1987) and Davis et al, Basic Methods of Molecular Biology, Elsevier Science Publishing Company, New York (1986) were used. Specifically, total RNA was prepared from bovine intermediate pituitaries as described in Chirgwin et al, Biochemistry, Vol. 18, pp. 5294–5299 (1979). Five ug of poly $(A)^+$RNA was used for synthesis of cDNA using the Amersham cDNA synthesis system. Gubler, et al, Gene, Vol. 25, pp. 263–269 (1983). Gel filtration was used to select cDNA segments larger than 500 base pairs in length. These were linked to 1 ug of lambda gt11 arms (Promega Biotech) and packaged using the Gigapack Gold™ in vitro lambda DNA packaging kit (Stratagene). A total of $2.3 \times 10^6$ recombinant phage were obtained; of the total phage, 11% were non-recombinant.

The recombinant phages were initially screened with the affinity purified PAM anti-serum described above. Six 150 mm dishes were plated at a density of $6.3 \times 10^4$ recombinant phage per dish. To identify phages which produced proteins which were reactive with the PAM anti-serum, the phages were induced with IPTG (isopropyl-beta-D-thioglactopyranoside) by application of IPTG-coated nitrocellulose filters to the phage plates for 8 hours. The filters were then washed for 0.5 hour at room temperature in TBS (50 mM Tris HCl, 150 mM NaCl, pH 7.5). The sites on the filter which did not contain protein were then blocked for one hour at room temperature in TBS containing 0.1 mg/ml bovine serum albumin and 0.1% Tween-20. The antiserum (Ab 36) was diluted in TBS/BSA plus Tween-20, applied to the filters, and the filters and antibodies were incubated overnight at 4° C. or for 4 hours at room temperature. The filters were then washed for 0.5 hour at room temperature in TBS/BSA plus Tween-20. Radioiodinated protein A ($10^5$ cpm/ml) in TBS/BSA was added to the filters for 2 to 4 hours at room temperature. The filters were washed for 10 minutes at room temperature in TBS/BSA, and then for 2×10 minutes in TBS/BSA containing 0.1% NP-40, and then for 10 minutes in TBS/BSA.

The sites of localization of the radioactivity were detected by autoradiography at –70° C. with an intensifying screen. Initially eighteen plaques were identified as positively reactive with the antiserum. Only six were positive upon rescreening, and the four phage which produced the strongest signals (lambda PAM-1, -2, -3, and -5) were further characterized.

Because the characterized recombinant phages lacked the 5' end of the gene, the cDNA library was screened to identify plaques containing the 5' end. This was done by hybridization of another aliquot of the library to nick translated fragments of lambda PAM-1 (the 0.4 kb and 0.7 kb fragments). Lambda PAM-6 was identified in this manner as a phage likely to contain the full length PAM cDNA.

FIG. 1 summarizes the structures of the cDNA clones obtained for phage identified with the affinity purified Ab 36 and with the cDNA probes. Plaque purified phage DNA was digested with EcoRI, and the sizes of the fragments released were determined by agarose gel electrophoresis. The EcoRI fragments of lambda PAM-1 were subcloned into Bluescript™ (Stratagene), nick translated and used to probe Southern blots of EcoRI digests of the other phages. The fragments were initially placed in 5' to 3' order based on the molecular weights of the fusion proteins produced in E. coli strain CAG456 and on the ability of synthetic oligonucleotides (shown below in Table 1) to hybridize with the restriction fragments. Phages lambda PAM-3a and lambda PAM-5a arose during the plaque purification of lambda PAM-3 and -5.

TABLE 1

Amino Acid Sequence Data for PAM and its Cyanogen Bromide Fragments

| Peptide | Sequence | Located in predicted prote |
|---|---|---|
| NH₂-terminal and B.E36B | PheLysGluThrThrArgSerPheSerAsnGluCysLeuGlyThr | 31–45 |
| NH₂-terminal and B.E38B | SerPheSerAsnGluCysLeuGlyThrThrArgProValIleProIleAsp | 37–53 |
| HR7 | ProGlyValThrProLysGlnSerAspThrTyrPheCys | 64–76 |
| B.F28 | AspGluGluAlaPheValIleAspPheLysProArgAlaSerThr | 84–97 |
| HR6 (OLIGO6) | MetMetSerValAspThrValIleProProGlyGlyLysValValAsnSerAspIleSerCysHisTyrLysLysTyrPr | 202–228 |
| CN2 (OLIGO8) | HisValPheAlaTyrArgValHisThrHisHisLeuGlyLysValValSerGlyTyrArg ValArgAsnGlyGlnTrpThrLeuIle | 230–258 |
| HR3 (OLIGO7) | GluAlaLysHisAlaValSerPheMetThrCysThrGlnAsnValAlaProAspIlePheArg | 319–339 |

For each analysis shown in Table 1, PAM was purified from 400 frozen bovine neurointermediate pituitaries (1). The NH₂-terminal sequence of PAM-B was determined for four different preparations; for the NH₂-terminal sequence, multiple residues were consistently found at every cycle. Data are consistent with the presence of the 2 major NH₂-terminal sequences indicated. In addition, approximately equivalent amounts of Glu and Tyr were consistently observed at position 41.

EXAMPLE 3

This example presents the complete nucleotide sequence of bovine PAM cDNA.

Subcloned EcoRI fragments of PAM cDNA were sequenced by the dideoxy-chain termination method of Sanger, et al, Proceedings of the National Academy of Sciences USA, Vol. 74, pp. 5463–5467 (1977); Biggin et al, Proceedings of the National Academy of Sciences USA, Vol. 80, pp. 3963–3965 (1983); Chen et al, DNA Vol. 4, pp. 165–170 (1985). Single stranded sequencing was performed as described by Stratagene. Double stranded sequencing was performed as described by New England Biolabs. To sequence the 2.2 kilobase EcoRI fragment of lambda PAM-1, nested sets of deletions extending inwards from the 5' and 3' termini of the cDNA were generated with an Exo III/Mung Bean Nuclease Kit from Stratagene. The sequencing strategies used for lambda PAM-1, -5 and -6 are indicated by the single headed arrows in FIG. 1, Part B. The relationship of the cyanogen bromide peptides sequenced and the synthetic oligonucleotides are also indicated by the hatched bars and line segments below the phage map. To sequence the 0.8 kilobase EcoRI fragment of lambda PAM-6, deletions with NdeI and NarI were prepared. The EcoRI site separating the 0.8 and the 0.7 kilobase fragments is in peptide HR6, and both EcoRI fragments hybridized with oligonucleotide No. 6. (See Table 1 for cyanogen bromide fragments and oligonucleotides.) The sequence across the EcoRI site separating the 0.7 and 2.2 kilobase fragments was obtained by subcloning the appropriate SspI-XbaI fragment and using a synthetic oligonucleotide primer. Synthetic oligonucleotide primers or deletions using unique restriction sites were used to direct sequencing to a particular region of the molecule. The nucleotide sequences obtained from lambda PAM-1, -5 and -6 have been used to construct the cDNA sequence and to predict the amino acid sequence. The entire molecule was sequenced on both strands of the DNA as diagramed in FIG. 1b. The amino acid sequence is numbered below the line from the initiator methionine (marked by a large downward arrow.) See FIG. 2. Amino acid residues which coincide with the peptide sequence information obtained from cyanogen bromide fragments are underlined. Pairs of basic amino acids are marked by a pair of dark triangles. Potential sites for N-linked glycosylation are indicated with dots. The poly-(A) addition signal is boxed. In lambda PAM-5, the 54 base pair segment for nucleotides 2823 to 2876 (shown in brackets) is absent.

FIG. 3 depicts the key features of the PAM cDNA sequence. The locations of the putative signal sequence and membrane spanning domain are indicated. All potential paired basic cleavage sites are indicated, as are the amino-termini and likely carboxy termini of PAM-A and PAM-B. The sequences of two histidine rich regions which are potentially involved in copper binding are also indicated. The standard one letter symbols for amino acids are used in this figure.

EXAMPLE 4

This example demonstrates the microbial expression of proteins which are reactive with PAM antibodies.

Ten ml cultures of *E. coli* strain CAG456 were infected with lambda gt11, lambda PAM-1, lambda PAM-2, or lambda PAM-3, and induction of the beta-galactosidase operon was accomplished with 10 mM IPTG; after 2 h at 37° C., cells were pelleted and dissolved in boiling SDS gel sample buffer (according to Laemmli, Nature, Vol. 227, pp. 680–685 (1970) containing phenylmethylsulfonyl fluoride (PMSF). About 5% of each sample was fractionated on 8% polyacrylamide slab gels, transferred to nitrocellulose and visualized with PAM Ab36 or a mouse monoclonal antibody reactive with beta-galactosidase and $^{125}$I-labeled Protein A. Visualization was accomplished by autoradiography.

The fusion proteins produced were clearly heterogeneous. The largest fusion protein produced had a molecular weight slightly greater than that of myosin, indicating that a PAM-related protein region of about 100,000 daltons was being produced. This is more than twice the size of the PAM proteins purified from bovine pituitary. The fusion protein was insoluble, even in the presence of solubilizing agents such as Triton X-100.

EXAMPLE 5

This example demonstrates that the fusion protein produced by lambda PAM-1 is in fact immunologically related to genuine PAM enzyme.

The enzyme depletion assay described above (Example 1) was used. For this experiment, the resin consisted of protein A-Sepharose to which fusion protein antibodies (see below) had been covalently cross-linked. In addition, means were devised to assay the enzyme activity bound to the resin as well as enzyme activity remaining in the supernatant.

Antibody directed against the fusion protein of lambda PAM-1 was produced by freezing and thawing the cell pellet from a 50 ml cultures of E. coli CAG456 infected with lambda PAM-1. The lysate was sonicated in 1.5 ml of 100 mM sodium TES, pH7.4, 10 mM EDTA, 1 mM PMSF, and centrifuged at 10,000×g for 10 minutes. Most of the fusion protein appeared in the pellet. The cell pellets were dissolved by boiling in 2 ml of SDS sample buffer and applied to Sephacryl S-300 SF columns. Fractions eluted from the column were analyzed by electrophoresis on polyacrylamide slab gels and visualized with Coomassie brilliant blue. The fractions from the column eluate which contained proteins ranging in size from that of myosin to beta-galactosidase were pooled and used for immunization of rabbits.

Three female New Zealand white rabbits (2 kilograms) were immunized with ⅙ of the fusion protein (0.5 $A_{280}$ units each) from a 50 ml culture emulsified in Freund's complete adjuvant. Rabbits were given five booster injections of the same amount of fusion protein in incomplete Freund's adjuvant at intervals of 2 to 4 weeks. Immunoglobulins from rabbit Ab46 were precipitated with ammonium sulfate, dialyzed into 3 M potassium thiocyanate, 0.1 M Tris HCl, pH7.2 and fractionated on a S-300 column in the same buffer. The fractions containing proteins larger than 80,000 daltons were dialyzed into 50mM NaTES, pH 7.4, and linked to protein A-Sepharose.

The pre-immune serum and antiserum Ab36 were not potassium thiocyanate-treated before linking to protein A-Sepharose. Without the potassium thiocyanate treatment, the resin prepared from Ab46 had 0.15 pmol/h PAM activity. The PAM activity in the Ab36 antiserum and the untreated Ab46 resins is thought to be due to circulating rabbit PAM bound to the circulating PAM antibodies.

Aliquots of PAM-A (0.95 pmol/h), PAM-B (0.65 pmol/h) or 100,000×g bovine neurointermediate pituitary supernatant (2.78 pmol/h) were incubated with protein A-Sepharose resin to which immunoglobulins from the anti-sera indicated in Table 2 had been covalently cross-linked. Enzyme activity bound to the resin was assayed in duplicate and varied less than plus or minus 15%. This experiment was repeated nine times in various forms with similar results.

TABLE 2

Binding of PAM Activity to Antibody Resins

| | PAM Activity (pmol/h) | | | | % Input Activity Bound to Resin | | |
|---|---|---|---|---|---|---|---|
| resin | buffer | PAM-A | PAM-B | pituitary supt | PAM-A | PAM-B | pituitary supt |
| pre-immune | .001 | .03 | .002 | .06 | 3 | 0.3 | 2 |
| Ab 36 (bovine PAM) | .78 | 1.07 | 1.00 | 1.58 | 31 | 34 | 29 |
| Ab 46 (β-gal-PAM fusion) | .001 | .55 | .16 | .52 | 58 | 25 | 19 |

As can be seen in the last row of Table 2, Ab46 (which was raised against the beta-galactosidase-PAM fusion protein) was able to bind and remove from the supernatant PAM activity which was isolated from bovine neurointermediate pituitary glands. This demonstrates that the lambda PAM clones do in fact contain sequences which code for PAM enzymes.

What is claimed is:

1. A recombinant DNA molecule which encodes a bovine peptidyl-glycine alpha-amidating monooxygenase (PAM) enzyme.

2. A DNA vector which encodes a bovine PAM enzyme.

3. A DNA vector of claim 2 wherein the PAM enzyme coding sequence is free of introns.

4. The DNA vector of claim 2 wherein the PAM enzyme is PAM-A.

5. The DNA vector of claim 2 wherein the PAM enzyme is PAM-B.

6. The DNA vector of claim 2 comprising the coding sequence of a pro-peptide of PAM.

7. A DNA vector which encodes a bovine PAM enzyme, said PAM enzyme comprising a membrane spanning domain.

8. A DNA vector which encodes a PAM enzyme, said vector comprising the coding sequence for the primary translation product of full length bovine PAM mRNA.

9. A method of producing a bovine PAM enzyme comprising:
   providing cultured cells which replicate and express an intron-free DNA sequence encoding a bovine PAM enzyme;
   growing said cultured cells; and
   recovering the PAM produced form said cultured cells.

10. The method of claim 9 wherein the PAM produced is selected from the group consisting of PAM-A, PAM-B, beta-galactosidase-PAM fusion proteins and the primary translation product of full length PAM mRNA.

11. The method of claim 9 wherein the cultured cells are prokaryotic.

12. The method of claim 9 wherein the cultured cells are eukaryotic.

13. A method of producing a bovine PAM enzyme comprising:
   providing cultured cells which replicate and express an intron-free DNA sequence encoding a bovine PAM enzyme, wherein said intron-free DNA sequence comprises a coding sequence for a membrane spanning domain;
   growing said cultured cells; and
   recovering the PAM produced form said cultured cells.

14. A method of producing a bovine PAM enzyme comprising:

providing cultured cells which replicate and express an intron-free DNA sequence encoding a bovine PAM enzyme, wherein said intron-free DNA sequence comprises a coding sequence for the primary translation product of full length bovine PAM mRNA;

growing said cultured cells; and recovering the PAM produced form said cultured cells.

15. An in vitro method of activating a peptide hormone precursor to a mature hormone having an alpha-amide group on the C-terminal amino acid residue comprising:

providing a peptide hormone precursor having a glycine residue on the C-terminal side of the C-terminal amino acid residue of the mature hormone; and contacting said peptide hormone precursor with a membrane preparation having PAM activity due to a bovine PAM enzyme to form an alpha-amidated derivative of the peptide.

16. The method of claim 15 wherein the membrane preparation is prepared from cultured cells which replicate and express the coding sequence of the primary translation product of full length PAM mRNA.

17. The method of claim 15 wherein the membrane preparation is prepared by incorporating a PAM enzyme having a membrane spanning domain into synthetic membranes.

18. The method of claim 15 wherein the membrane preparation is prepared from cultured cells which replicate and express an intron-free DNA sequence of a PAM enzyme.

19. A bovine PAM protein, including a membrane spanning domain and being substantially free of proteins which do not have PAM activity.

20. Culture cells which have been transformed with a vector which encodes a bovine PAM enzyme.

21. The cultured cells of claim 20 which have been transformed with an intron-free DNA sequence of a PAM enzyme.

22. The cells of claim 20 which are prokaryotic.

23. The cells of claim 20 which are yeast cells.

24. The cells of claim 20 which are mammalian.

25. The cells of claim 20 which are avian.

26. Cultured cells which have been transformed with a vector which encodes a bovine PAM enzyme, wherein the PAM enzyme includes a membrane spanning domain.

27. A method of producing a bovine PAM enzyme comprising:

providing cultured cells which replicate and express and intron-free DNA sequence encoding a bovine PAM enzyme;

growing said cultured cells in a culture medium; and recovering the PAM enzyme from the culture medium.

28. A purified protein selected from the group consisting of bovine pre-PAM and bovine prepro-PAM.

* * * * *